(12) United States Patent
Morimoto (10) Patent No.: US 10,139,624 B2
(45) Date of Patent: Nov. 27, 2018

(54) HEAD MOUNTED DISPLAY, CONTROL DEVICE, AND CONTROL METHOD

(71) Applicant: SONY CORPORATION, Tokyo (JP)

(72) Inventor: Toshiyasu Morimoto, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/118,367

(22) PCT Filed: Jan. 8, 2015

(86) PCT No.: PCT/JP2015/050318
§ 371 (c)(1),
(2) Date: Aug. 11, 2016

(87) PCT Pub. No.: WO2015/125508
PCT Pub. Date: Aug. 27, 2015

(65) Prior Publication Data
US 2017/0168297 A1    Jun. 15, 2017

(30) Foreign Application Priority Data
Feb. 21, 2014  (JP) .................................. 2014-032009

(51) Int. Cl.
| | |
|---|---|
| *G02B 27/01* | (2006.01) |
| *A61B 1/00* | (2006.01) |
| *G02B 27/02* | (2006.01) |
| *G06T 19/00* | (2011.01) |
| *H04N 5/74* | (2006.01) |

(52) U.S. Cl.
CPC ........ *G02B 27/017* (2013.01); *A61B 1/00048* (2013.01); *G02B 27/0179* (2013.01); *G02B 27/022* (2013.01); *G06T 19/00* (2013.01); *H04N 5/7491* (2013.01)

(58) Field of Classification Search
None
See application file for complete search history.

(56) References Cited

U.S. PATENT DOCUMENTS

| | | | | |
|---|---|---|---|---|
| 5,949,388 A | * | 9/1999 | Atsumi | ............. G02B 27/0172 345/53 |
| 6,847,336 B1 | | 1/2005 | Lemelson et al. | |
| 2002/0113907 A1 | * | 8/2002 | Endo | ..................... G09G 5/006 348/730 |

(Continued)

FOREIGN PATENT DOCUMENTS

| | | |
|---|---|---|
| JP | 06-062438 A | 3/1994 |
| JP | 10-201700 A | 8/1998 |

(Continued)

OTHER PUBLICATIONS

Extended European Search Report of EP Application No. 15752719.3, dated Sep. 21, 2017, 07 pages of EESR.

*Primary Examiner* — Nicholas Lee
(74) *Attorney, Agent, or Firm* — Chip Law Group (57) ABSTRACT

To improve communication between a wearer of a Head Mount Display (HMD) while wearing the HMD and a non-wearer of the HMD, provided is a head mounted display, including a display unit configured to present an image to a wearer, a mounting unit configured to be mounted on a head of the wearer, and a notification unit configured to notify a person other than the wearer of information that the wearer is visually recognizing.

10 Claims, 9 Drawing Sheets

(56) References Cited

U.S. PATENT DOCUMENTS

| | | | | |
|---|---|---|---|---|
| 2006/0238877 A1* | 10/2006 | Ashkenazi | ......... | G02B 27/0093 |
| | | | | 359/630 |
| 2009/0243966 A1* | 10/2009 | Kato | .................... | G02B 27/017 |
| | | | | 345/8 |
| 2013/0241805 A1 | 9/2013 | Gomez | | |
| 2015/0331451 A1* | 11/2015 | Shin | ........................ | G06F 3/041 |
| | | | | 345/173 |

FOREIGN PATENT DOCUMENTS

| | | |
|---|---|---|
| JP | 2001-104331 A | 4/2001 |
| JP | 2001-290103 A | 10/2001 |
| JP | 2009-229859 A | 10/2009 |
| JP | 2013-106752 A | 6/2013 |
| WO | 2012/062872 A1 | 5/2012 |
| WO | 2014/103193 A1 | 7/2014 |

\* cited by examiner

HEAD MOUNTED DISPLAY, CONTROL DEVICE, AND CONTROL METHOD

CROSS REFERENCE TO RELATED APPLICATIONS

This application is a U.S. National Phase of International Patent Application No. PCT/JP2015/050318 filed on Jan. 8, 2015, which claims priority benefit of Japanese Patent Application No. JP 2014-032009 filed in the Japan Patent Office on Feb. 21, 2014. Each of the above-referenced applications is hereby incorporated herein by reference in its entirety.

TECHNICAL FIELD

The present invention relates to a head mounted display that a user wears on his/her head and uses, a control device for controlling a head mounted display, and a control method.

BACKGROUND ART

As one of wearable terminals that a user wears and uses, there is a head mounted display (hereinafter, referred to as "HMD"). The HMD is a display device that is mounted on the head of a user when used and in recent years, the HMD is not only used as AV equipment and a display device for a computer game and the like. but also used as a display device for a user to check information while working in working environment.

For example, on a medical site, the HMD is used as a display device for displaying an image of an endoscope (for example, Patent Literatures 1 and 2). An operator wears the HMD and performs an operation while viewing an image displayed on the HMD. In the past, an image of the endoscope was usually displayed on a monitor installed in the vicinity of the operator, and therefore, it was necessary for the operator to frequently move his/her visual line between the monitor and a patient. By displaying the image of the endoscope on the HMD, it is made possible for an operator to check the image of the endoscope displayed on the display unit of the HMD and a patient without moving his/her visual line considerably.

CITATION LIST

Patent Literature

Patent Literature 1: JP H06-062438A
Patent Literature 2: JP 2013-106752A

SUMMARY OF INVENTION

Technical Problem

However, when an HMD of a type that covers the eyes of a person who wears the HMD is used, it is not possible to recognize peripheral environment, and therefore, it becomes difficult to establish communications during the operation, such as giving instructions to an assistant or a nurse. In contrast to this, it is conceivable to use an HMD of a video see-through type that mounts a camera on the HMD to allow viewing peripheral environment. If a video see-through function is added to the HMD, an operator who is wearing the HMD is enabled to recognize the situations of staffs around the operator by switching between the endoscope image and external camera image during the operation, and therefore, it is conceivable that communication will be improved.

However, there is a case where a scopist (endoscope operator) and an assistant also wear the HMD, besides the operator. In the case such as this where a plurality of persons wear the HMDs and perform an operation in collaboration, it is possible to recognize peripheral environment by video see-through, but it is not possible to recognize what another person wearing the HMD is viewing. Because of this, there is a possibility that a loss in cooperation will occur between operators.

Consequently, the improvement in communication with another person when the HMD is mounted has been demanded.

Solution to Problem

According to the present disclosure, there is provided a head mounted display, including a display unit configured to present an image to a wearer, a mounting unit configured to be mounted on a head of the wearer, and a notification unit configured to notify a person other than the wearer of information that the wearer is visually recognizing.

According to the present disclosure, there is provided a control device, including a visually recognized information acquisition unit configured to acquire information that a wearer of a head mounted display is visually recognizing, and a notification control unit configured to control a notification unit on a basis of information that the wearer is visually recognizing, the notification unit being included in the head mounted display and notifying a person other than the wearer of information that the wearer is visually recognizing.

According to the present disclosure, there is provided a control method, including acquiring information that a wearer of a head mounted display is visually recognizing, and controlling a notification unit on a basis of information that the wearer is visually recognizing, the notification unit being included in the head mounted display and notifying a person other than the wearer of information that a wearer is visually recognizing.

According to the present disclosure, a person other than the wearer is notified of information visually recognized by a wearer wearing a head mounted display by a notification unit. In this way, the person other than the wearer can recognize what the wearer is viewing.

Advantageous Effects of Invention

According to the present disclosure, information that a wearer of a head mounted display is visually recognizing can be recognized by a non-wearer or another wearer, which can improve the communication with other persons when each person wears the head mounted display.

The above-described effect is not necessarily limitative and it may also be possible to bring about any effect shown in the present specification or another effect that can be grasped from the present specification together with or in place of the above-described effect.

DESCRIPTION OF EMBODIMENT(S)

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that the description will be given in the following order.
1. First Embodiment
  1.1. System configuration
  1.2. Notification unit
  1.3. Display control processing
  1.4. Summary
2. Second embodiment (example including visual line detection unit)
3. Modified examples 1. First Embodiment

[1.1. System Configuration]

Figure 1:
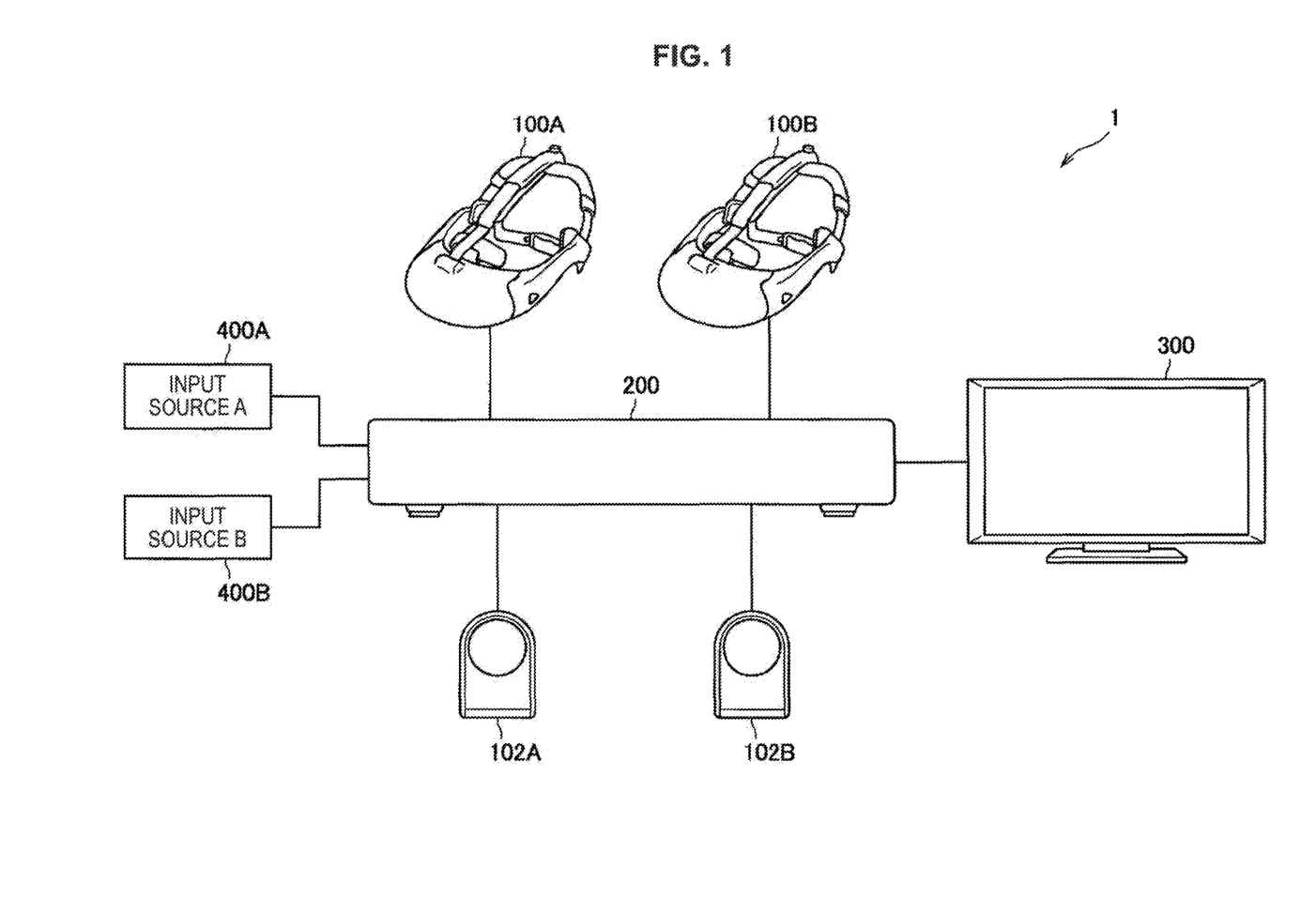
FIG. 1 is a system configuration diagram showing a configuration example of an endoscope system according to a first embodiment of the present disclosure.
Figure 2:
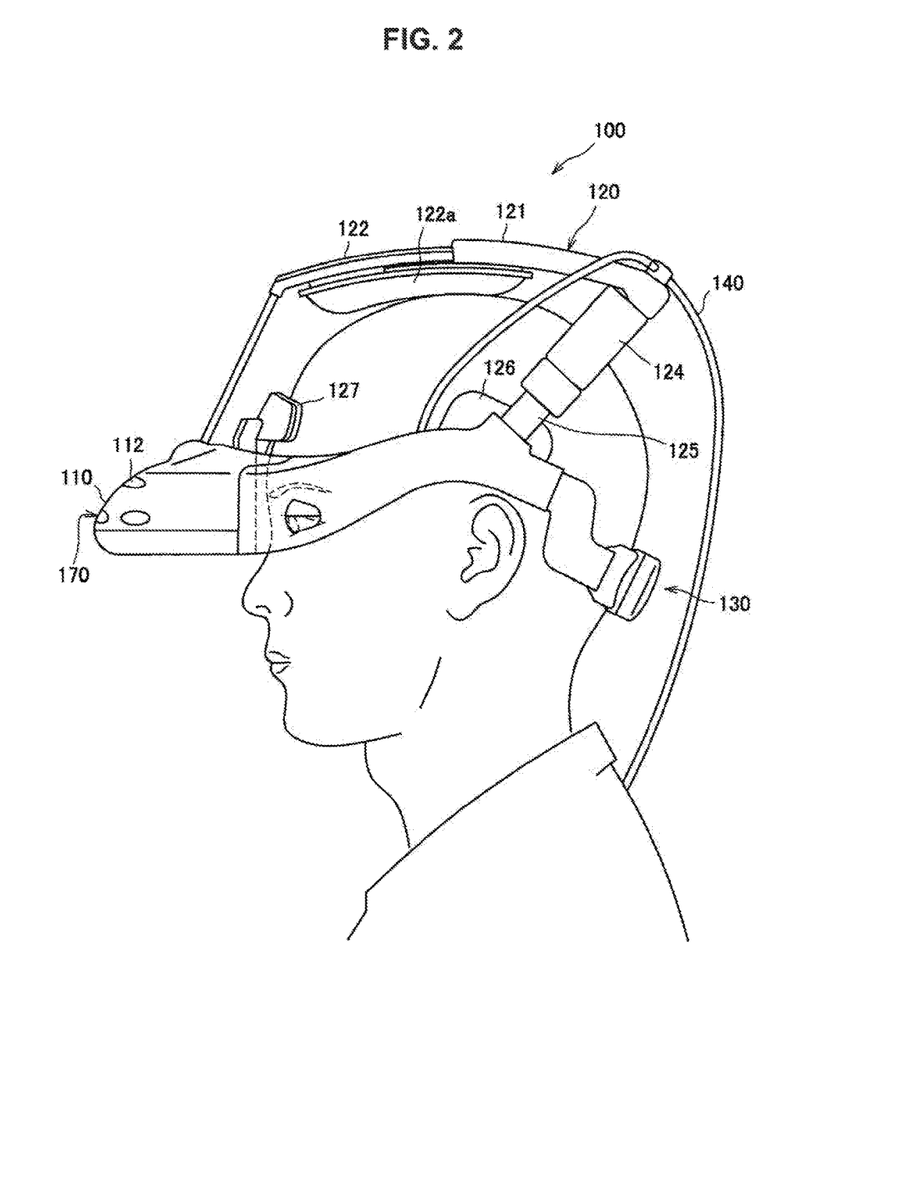
FIG. 2 is a schematic side view showing a state where a user wears an HMD according to the same embodiment.
Figure 3:
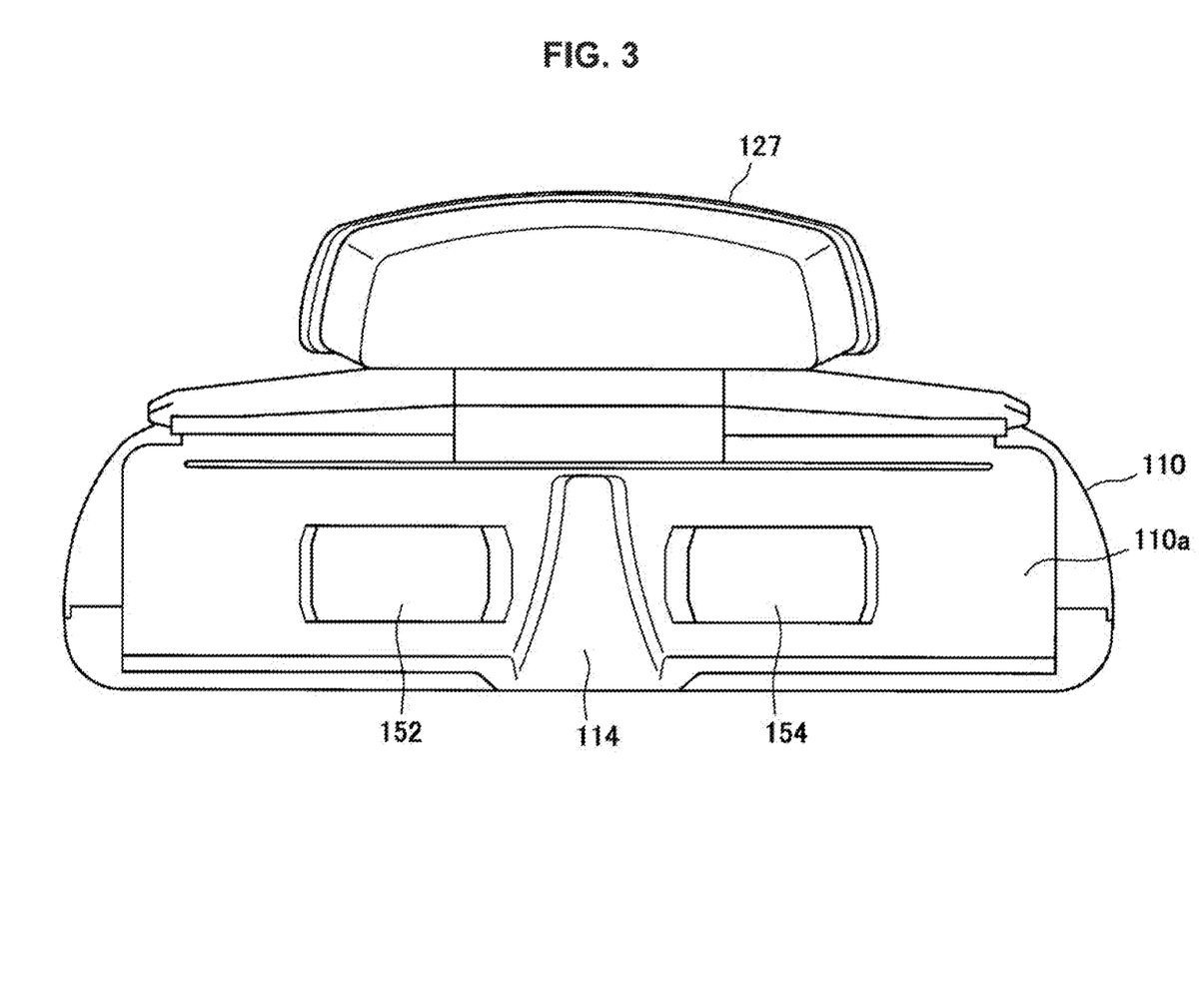
FIG. 3 is a schematic diagram showing a display plane of the HMD according to the same embodiment.

First, with reference to FIG. 1 to FIG. 3, as an example of a system that uses an HMD according to a first embodiment of the present disclosure, an endoscope system is described. FIG. 1 is a system configuration diagram showing a configuration example of an endoscope system 1 according to the present embodiment. FIG. 2 is a schematic side view showing a state where a user wears an HMD 100 according to the present embodiment. FIG. 3 is a schematic diagram showing display planes 152 and 154 of the HMD 100.

Note that the present disclosure defines users using the endoscope system 1 as follows.

"Wearer": a person wearing an HMD.

"Non-wearer": a person not wearing an HMD.

Further, in the case where there are a plurality of "wearers", a wearer (/wearers each) wearing an HMD other than one "wearer" may also be referred to as "another wearer (/other wearers)".

The endoscope system 1 according to the present embodiment is a system used in an endoscopic operation and an operator wears an HMD and performs an operation while visually recognizing the state of an affected area the image of which is captured by an endoscope device.

As shown in FIG. 1, the endoscope system 1 has a configuration in which HMDs 100 (100A, 100B), a display 300, and external devices 400 (400A, 400B) are connected to a processor unit 200.

The HMD 100 is a display device that displays information, such as an input image from the external device 400. As shown in FIG. 2, the HMD 100 is, for example, a non-transmissive HMD in the shape of goggles and is used in a state of being mounted on the head of a user. The HMD 100 includes a main body unit 110 including the display units 152 and 154 for presenting information to a wearer of the HMD 100, and an upper fixing unit 120 and a rear fixing unit 130 for fixing the main body unit 110 to the head. When the HMD 100 is fixed to the head of the wearer by the fixing units, the display units 152 and 154 of the main body unit 110 are located in front of the left and right eyes of the wearer.

The main body unit 110 is a portion that covers both the eyes of the wearer. The main body unit 110 may be configured so as to cover, for example, the parts in the vicinity of the left and right temples of the wearer. By forming the main body unit 110 into such a shape, it is possible to cover the parts in front of the eyes of the wearer almost perfectly when the wearer wears the HMD 100, and therefore, it is made possible for the wearer to easily view an image because no external light enters the wearer's eyes. An image capturing unit 112 configured to shoot, for example, peripheral environment, may be provided on the external surface of the main body unit 110. Due to this, the wearer wearing the HMD 100 can also recognize information on peripheral environment that is seen when the HMD 100 is not mounted (video see-through), in addition to information provided from the external device 400 and the like via the processor unit 200.

At an eyepiece plane 110a of the main body unit 110, as shown in FIG. 3, a first display unit 152 for the left eye and a second display unit 154 for the right eye are provided so as to correspond to the positions of the left and right eyes of the wearer. Between the first display unit 152 and the second display unit 154, for example, a cutout for positioning the nose of the wearer may be formed. A gap may be provided between the eyepiece plane 110a of the main body unit 110 and the wearer's eyes. By opening the lower part of the gap without covering it, the wearer may see his/her own hands and the like when the wearer lowers his/her visual line.

Inside the main body unit 110, a first display element (reference numeral 165 in FIG. 4) that presents an image for the left eye on the first display unit 152 and a second display element (reference numeral 166 in FIG. 4) that presents an image for the right eye on the second display unit 154 are provided. Each display element presents, for example, an image of the endoscope device provided by the processor unit 200, an image captured by the image capturing unit 112 of the main body unit 110, and the like. Display control processing of an image that is displayed on the display unit of the HMD 100 will be described later. The main body unit 110 is also provided with a cable 140 that is connected to the processor unit 200 in order to perform transmission and reception of information with the processor unit 200. In the present embodiment, the HMD 100 and the processor unit 200 are connected by a wire, but the present disclosure is not limited to this example and communication of information between devices may be performed wirelessly.

The upper fixing unit 120 supports the main body unit 110 from the upper part of the head of the wearer in order to fix the main body unit 110 to the position of the wearer's eyes. The upper fixing unit 120 includes support units 121 and 124 located at the parietal region of the head, a first adjustment unit 122 configured to adjust the position on the wearer's front side, and a second adjustment unit 125 configured to adjust the height position on the left and right sides of the wearer.

As shown in FIG. 2, the first adjustment unit 122 is a member that couples the upper part of the main body unit 110 and the support unit 121 and is configured so that the length thereof can be adjusted. By adjusting the length of the first adjustment unit 122, the degree with which a forehead contact pat 127 installed above the eyepiece plane 110a of the main body unit 110 is pressed against the forehead of the wearer is changed, which enables to adjust the position on the wearer's front side.

As shown in FIG. 2, the second adjustment unit 125 is a member that couples both sides of the main body unit 110, which extend toward the upper part of the left and right ears of the wearer when the HMD 100 is mounted, and the support unit 124, and is configured so that the length thereof can be adjusted. The second adjustment units 125 are provided on the left side and on the right side, respectively. By adjusting the length of the second adjustment unit 125, a head pat 122a installed between the first adjustment unit 122 and the head is pressed against the wearer's head and thereby the height positions of both the side parts of the main body unit 110 are adjusted.

The rear fixing unit 130 supports the main body unit 110 from the back of the wearer's head in order to fix the main body unit 110 at the position of the wearer's eyes. As shown in FIG. 2, the rear fixing unit 130 is a member that couples both sides of the main body unit 110 on the back side of the head and is configured so that the length thereof can be adjusted. By adjusting the length of the rear fixing unit 130, the degree with which side pats 126 provided on both sides of the main body unit 110 are pressed against the head is changed, which enables to adjust the support degree at the temporal region.

It may also be possible to switch information displayed on the display units 152 and 154 of the HMD 100 by a remote controller 102 (102A, 102B). The remote controller 102 is provided so as to form a pair with one HMD 100. For example, the remote controller may be a foot switch that a wearer steps on by the wearer's foot to perform an input operation. Input information from the remote controller 102 is output to the processor unit 200.

The processor unit 200 is a control device that controls connected devices. In the present embodiment, the processor unit 200 controls the HMDs 100 (100A, 100B), the display 300, and the external devices 400 (400A, 400B) as shown in FIG. 1. Specifically, the processor unit 200 processes information input from the external device 400 into information that can be displayed on the display devices of the HMDs 100 and the display 300, and outputs the information to each display device. Further, the processor unit 200 switches information displayed on the display units 152 and 154 of the HMD 100 based on the operation input from the remote controller 102 of each HMD 100.

The display 300 is a display device for an unspecified user to view information. The display 300 is mainly used for a non-wearer not wearing the HMD 100, who works together with wearers each wearing the HMD 100, to view information. The display 300 can display information input from the external device 400 and other pieces of information. Information displayed on the display 300 is set by a wearer, a non-wearer, or the processor unit 200.

The external device 400 is a device that outputs information displayed on the display device, such as the HMD 100 and the display 300. In the endoscope system 1 of the present embodiment, for example, the external device A400A is an endoscope device and an image captured by the camera of the endoscope device is output to the processor unit 200.

In the endoscope system 1 such as this, information input from the external device 400 is processed by the processor unit 200 and is displayed on the display device, such as the HMD 100 and the display 300.

[1.2. Notification Unit]

In the case where the HMD 100 according to the present embodiment is capable of performing switching between multiple pieces of information to be displayed on the display units 152 and 154, it is not possible for a person other than the wearer of the HMD 100 to recognize what the wearer is viewing, since the wearer's eyes are covered with the main body unit 110. Accordingly, the HMD 100 according to the present embodiment includes, on the external surface of the main body unit 110, a notification unit 170 configured to show information that the wearer of the HMD 100 is visually recognizing. The notification unit 170 may be provided at a position at which a person other than the wearer of the HMD 100 can visually recognize. The notification unit 170 may be configured as shown in FIGS. 4 to 7, for example.

Figure 4:
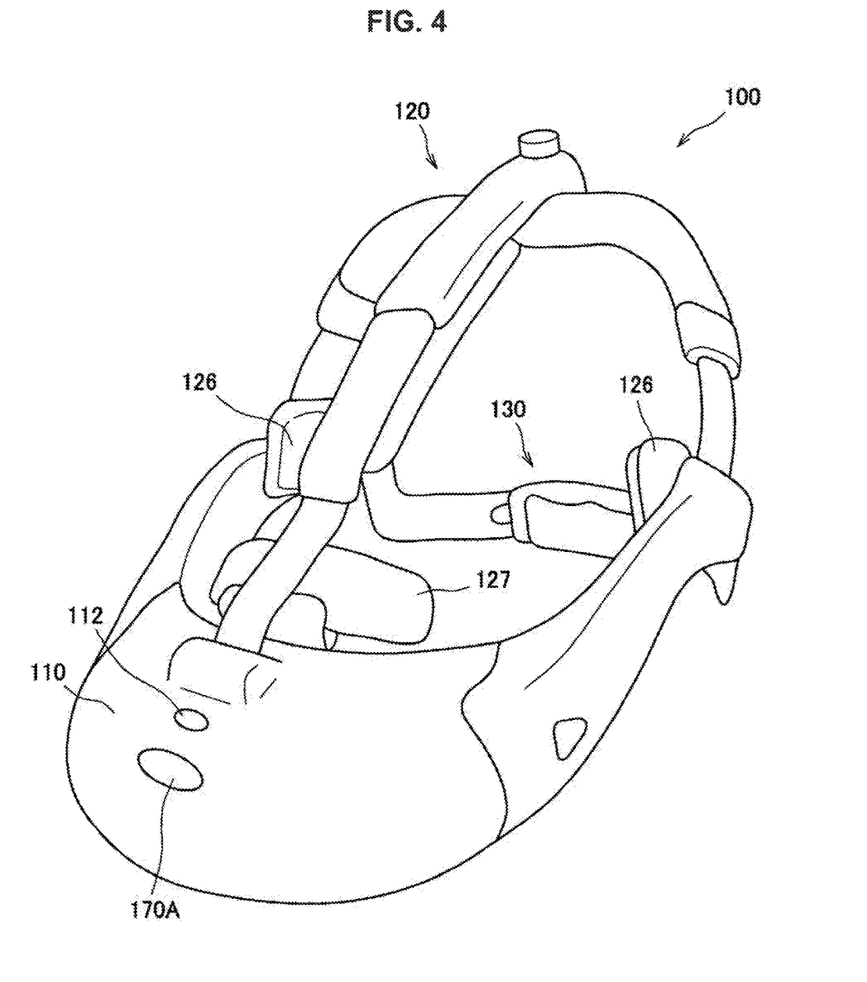
FIG. 4 is an explanatory diagram showing a configuration example of a notification unit provided in the HMD according to the same embodiment, the notification unit including one lamp.

A notification unit 170A shown in FIG. 4 includes one lamp provided in the vicinity of the center of the external surface of the main body unit 110. The lamp may be an LED lamp, for example. The lighting state of the lamp is controlled depending on information that the wearer of the HMD 100 is visually recognizing. Examples of the lighting state include lighting-on, lighting-off, and blinking. For example, the lamp is controlled in a manner that the lamp is on in the case where the wearer views information of the external device A400A, the lamp is blinking in the case where the wearer views information of the external device B400B, and the lamp is off in the case where the wearer views peripheral environment using the image capturing unit 112. Alternatively, the amount of light emitted from the lamp may be changed depending on information that the wearer of the HMD 100 is visually recognizing.

Figure 5:
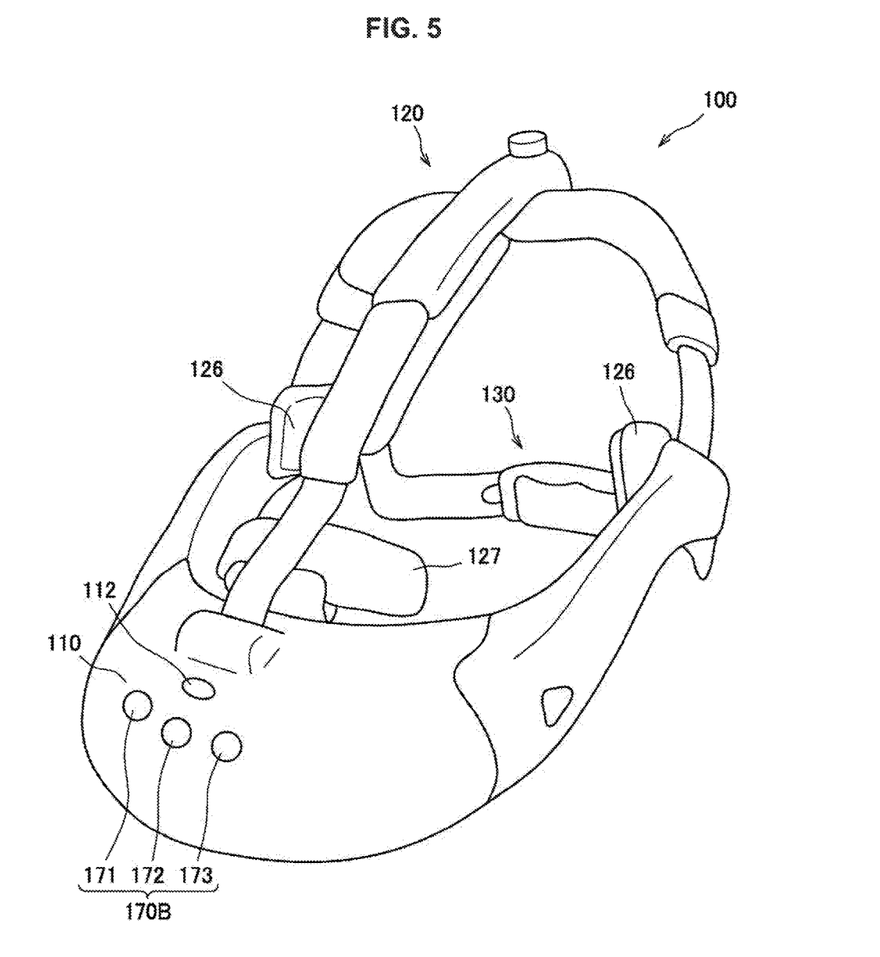
FIG. 5 is an explanatory diagram showing a configuration example of a notification unit provided in the HMD according to the same embodiment, the notification unit including three lamps having a same color.

A notification unit 170B shown in FIG. 5 includes three lamps, lamps 171, 172, and 173, which are provided in the vicinity of the center of the external surface of the main body unit 110. The lamps 171, 172, and 173 may also be LED lamps. In the case where the lamps 171, 172, and 173 each have a same color, pieces of information displayable on the display units 152 and 154 (or input terminals of the processor unit 200) are each associated with a lamp to be turned on, and a corresponding lamp may be turned on depending on information that the wearer of the HMD 100 is visually recognizing.

Note that, although it is simple to understand if pieces of information and the lamps are in one-to-one correspondence, the number of lamps may be smaller than the number of pieces of displayable information. In this case, the lighting state of each lamp may be changed and thus can show the difference between the pieces of information. Alternatively, the number of lighting-on lamps may be changed and thus can also show the difference between the pieces of information. For example, one lamp, the lamp 171, may be turned on in the case where the wearer views the information of the external device A400A, and two lamps, the lamps 171 and 172, may be turned on in the case where the wearer views the information of the external device B400B.

Figure 6:
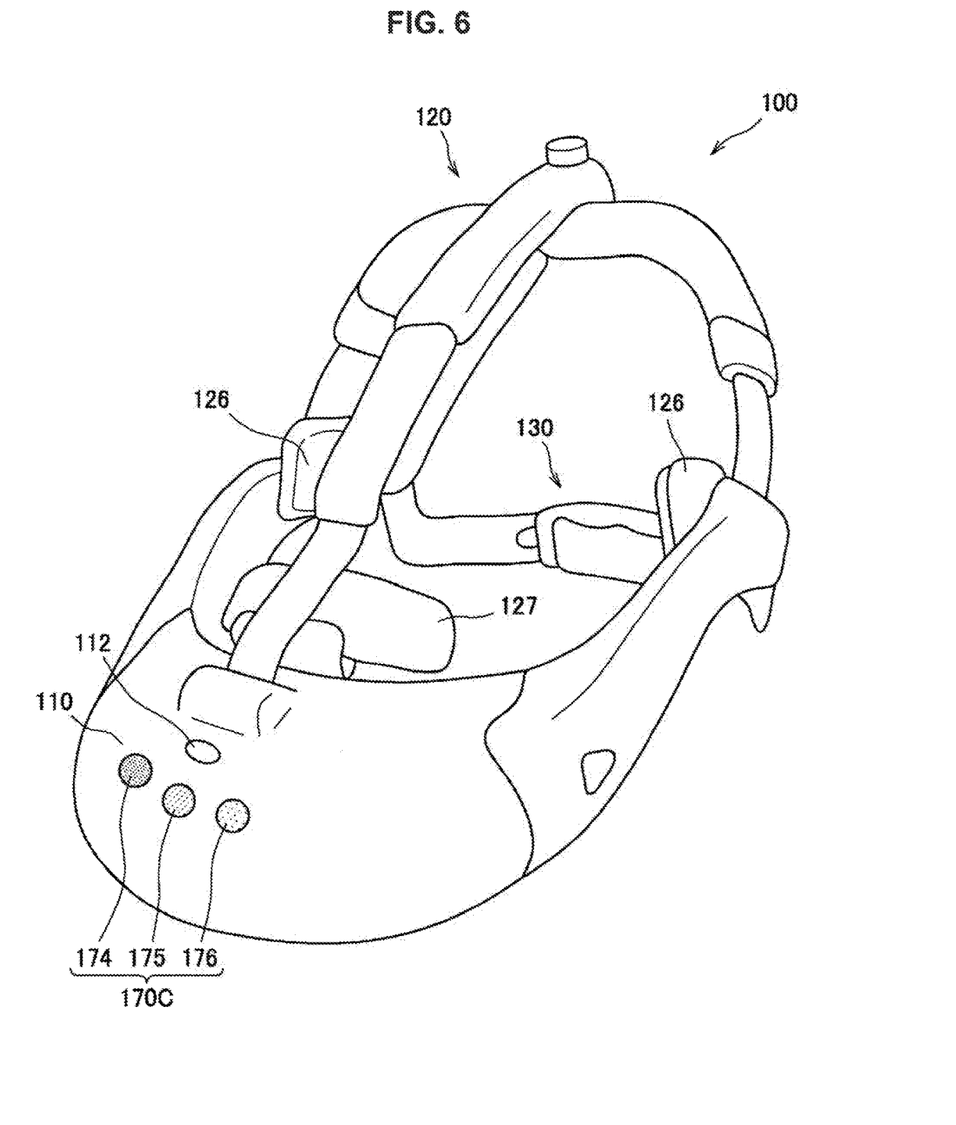
FIG. 6 is an explanatory diagram showing a configuration example of a notification unit provided in the HMD according to the same embodiment, the notification unit including three lamps each having a color different from each other.

A notification unit 170C shown in FIG. 6 includes three lamps, lamps 174, 175, and 176 each having a color different from each other, which are provided in the vicinity of the center of the external surface of the main body unit 110. The lamps 174, 175, and 176 may also be LED lamps. In this way, the lamps 174, 175, and 176 each having a color different from each other may be used to notify a non-wearer of information in a simple manner. Note that, in the same manner as the notification unit 170B shown in FIG. 5, in the notification unit 170C shown in FIG. 6, pieces of information and the lamps are not necessarily be in one-to-one correspondence, and the lighting state and the number of lighting-on lamps may be changed and thus can show the difference between the pieces of information.

Figure 7:
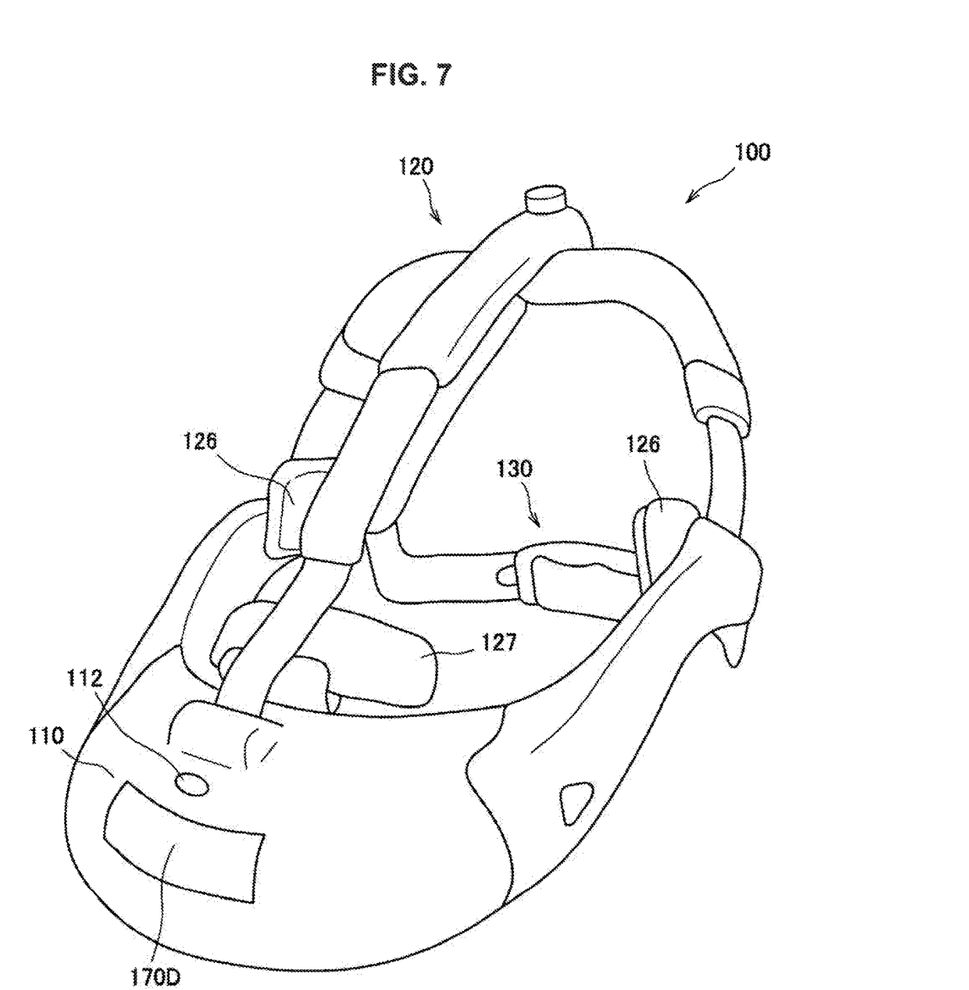
FIG. 7 is an explanatory diagram showing a configuration example of a notification unit provided in the HMD according to the same embodiment, the notification unit including a display device.

A notification unit 170D shown in FIG. 7 is a display device which displays information that the wearer of the HMD 100 is visually recognizing. Examples of the display device include a liquid crystal display, an organic EL display, a lightweight display device such as electronic paper, and a display device which can be curved so as to be capable of being placed on a curved surface. Information to be displayed on the display device may be information itself that the wearer of the HMD 100 is actually visually recognizing, or may be corresponding information representing the information. Examples of the corresponding information include a thumbnail, text information, and a chart. In this way, a non-wearer can easily recognize the information that the wearer of the HMD 100 is visually recognizing by viewing the notification unit 170D.

Note that the form of the notification unit 170 of the HMD 100 according to the present embodiment is not limited to the examples described above. Further, the forms of the above-mentioned notification units 170A to 170D can be combined with each other as appropriate, for example, a lamp and a display device may be provided in combination.

[1.3. Display Control Processing]

While the wearer of the HMD 100 performs an operation, the wearer performs switching between a medical image presented from the processor unit 200 and an image shot by the image capturing unit 112 of the HMD 100. In this case, the HMD 100 has information of the external device 400 and the like displayed on the display units 152 and 154, and is also notified of information that the wearer of the HMD 100 is visually recognizing by the notification unit 170 of the main body unit 110. Hereinafter, with reference to FIG. 8, there will be described information display control and notification control on the HMD 100 of the endoscope system 1 according to the present embodiment.

Figure 8:
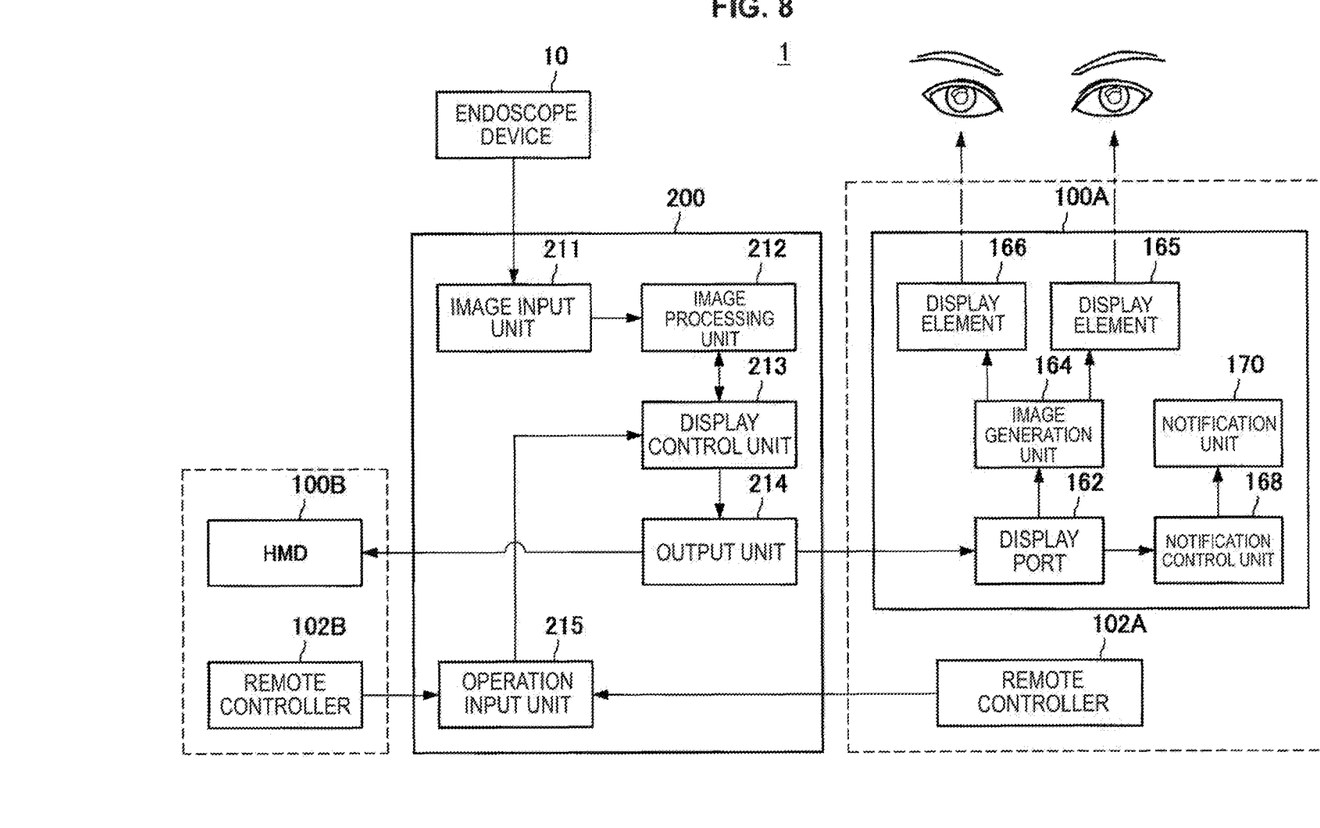
FIG. 8 is a function block diagram showing a function configuration of the HMD and a processor unit constituting a display control system according to the same embodiment.

FIG. 8 shows a function configuration of the HMD 100 and the processor unit 200 constituting the endoscope system 1 according to the present embodiment. In FIG. 8, the function units that function when display control of the display units 152 and 154 of the HMD 100 is performed and a notification control function of the HMD 100 are shown and it is assumed that other function units are also included actually. In the example in FIG. 8, the processor unit 200 functions as a display control device that performs display control of the two HMDs 100A and 100B and based on instructions to switch displays of each of the HMDs 100A and 100B, information presented on each of the HMDs 100A and 100B is switched.

First, referring to the display processing functions of the HMD 100, as shown in FIG. 8, the HMD 100 includes a display port 162, an image generation unit 164, display elements 165 and 166, and a notification control unit 168.

The display port 162 is an interface that receives input information from the processor unit 200. To the display port 162, the cable 140 that enables information communication with the communication unit 200 is connected. Input to the display port 162 are, for example, image signals to be output to the display elements 165 and 166, respectively, and information visually recognized by a wearer of the HMD 100. The information input from the display port 162 is output to the image generation unit 164.

The image generation unit 164 generates image signals that are output to the display elements 165 and 166, respectively, based on the information acquired via the processor unit 200. In the case where the image presented to a wearer is a 3D image, the image generation unit 164 performs shift processing to produce a shift between a left-eye image signal that is output to the first display element 165 and a right-eye image signal that is output to the second display element 166. In the shift processing, for example, the amount of shift between the left-eye image signal and the right-eye image signal is determined in accordance with, for example, the distance between the display elements 165 and 166 and the wearer's eyes, the interval between wearer's eyes, the virtual image position, and the like. The image generation unit 164 outputs the generated image signal to the first display element 165 and the second display element 166.

The display elements 165 and 166 emit image light toward the display units 152 and 154 based on the image signal input from the image generation unit 164. The display elements 165 and 166 are arranged, for example, so as to face the display units 152 and 154 in the longitudinal direction of the wearer's face when the HMD 100 is mounted. Due to this, the optical axis of the image light emitted from the display elements 165 and 166 and the display units 152 and 154 will become substantially parallel to the direction of the visual line when the wearer faces the front.

The display elements 165 and 166 include, for example, an organic electroluminescence (EL) element. By adopting the organic EL element as the display elements 165 and 166, it is possible to realize compactness, high contrast, quick responsiveness, and the like. The display elements 165 and 166 have a configuration in which, for example, a plurality of red organic EL elements, a plurality of green organic EL elements, a plurality of blue organic EL elements, and the like, are arranged in the form of a matrix. Each of these elements spontaneously emits light at predetermined timing, luminance, and the like, by being driven by a drive circuit of active matrix type, passive matrix type, and the like. By controlling the drive circuit based on the image signal generated in the image generation unit 164, a predetermined image is displayed on the entire display elements 165 and 166 and the display is presented to a wearer via the display units 152 and 154.

Between the display elements 165 and 166 and the display units 152 and 154, as an optical system, for example, a plurality of eyepiece lenses (not shown) may be arranged, respectively. By causing these eyepiece lenses and the wearer's eyes to face each other with a predetermined distance in between, it is made possible to cause a wearer to observe a virtual image, which looks as if an image is displayed at a predetermined position (virtual image position). By presenting such a virtual image, it is possible to provide a 3D image. The virtual image position and size of the virtual image are set by the configuration and the like of the display elements 165 and 166 and the optical system.

In order to cause a wearer to observe a virtual image, the main body unit 110 is mounted on the user so that image light emitted in the optical axis direction from the display elements 165 and 166 forms an image on the retinas of the left and right eyes, respectively. In the case where the main body unit 110 is not mounted appropriately, the image will be a blurred image out of focus or a deviation occurs in the 3D image, and therefore, the wearer is not able to view a desired image. Consequently, when wearing the HMD 100, a user fixes the main body unit 110 to the head by the upper fixing unit 120 and the rear fixing unit 130 so that a relevant position is not shifted after adjusting the main body unit 110 to an appropriate position.

The notification control unit 168 controls the notification unit 170 on the basis of input information from the processor unit 200 that is input to the display port 162. The notification control unit 168 controls the notification unit 170 in a manner that the notification unit 170 shows information to be newly displayed at the timing of switching of display information on the display units 152 and 154, for example. In the case where the notification unit 170 includes lamp(s), for example, the notification control unit 168 controls the lighting state of the lamp(s), the number of lighting-on lamps, and the amount of light emitted from the lamp(s). Further, in the case where the notification unit 170 includes a display device, for example, the notification control unit 168 displays information to be displayed on the display device, or corresponding information that corresponds to the information, the corresponding information including a thumbnail, text information, or a chart.

Note that the notification control unit 168 may perform, by the notification unit 170, notification that the display of the HMD 100 is switched. In the case where the notification unit 170 includes lamp(s), for example, the notification control unit 168 may perform control in a manner that the lamp is turned on in a lighting pattern that shows switching of display and then the lamp is brought to a lighting state corresponding to information to be displayed after the switching. Further, in the case where the notification unit 170 includes a display device, for example, the notification control unit 168 may cause a thumbnail that is displayed on the display device to be temporarily displayed in a blinking manner, or may cause an alarm that shows the switching of the display to be displayed.

Next, referring to the display processing functions of the processor unit 200, as shown in FIG. 8, the processor unit 200 includes an image input unit 211, an image processing unit 212, a display control unit 213, an output unit 214, and an operation input unit 215.

The image input unit 211 is an interface that receives an image input to the processor unit 200 from the external device 400. In the example shown in FIG. 8, the endoscope device 10 is shown as the external device 400, and at this time, to the image input unit 211, an image captured by the camera (not shown) of the endoscope device 10 is input. The image input unit 211 outputs the image input to the image processing unit 212.

The image processing unit 212 processes an image input to the processor unit 200 into an image to be displayed on the HMD 100. The image processing unit 212 generates a left-eye image to be displayed on the first display unit 152 of the HMD 100 and a right-eye image to be displayed on the second display unit 154 from, for example, an image captured by the camera of the endoscope device 10. The image on which image processing has been performed by the image processing unit 212 is output to the display control unit 213.

The display control unit 213 controls information to be displayed by the display units 152 and 154 of the HMD 100. The display control unit 213 performs control in a manner that, on the basis of instructions to switch displays from the remote controller 102, specified information is displayed. When the display control unit 213 determines the information to be displayed by each HMD 100, the display control unit 213 outputs the information to each HMD 100 via the output unit 214.

The operation input unit 215 is an input unit that receives an operation input from a wearer of the HMD 100. In the present embodiment, information to be displayed on the display units 152 and 154 of the HMD 120 can be switched by the remote controller 102. An operation input to the remote controller 102 is output to the operation input unit 215 and the operation input unit 215 outputs the operation input information to the display control unit 213. The display control unit 213 outputs specified information to the HMD 100 via the output unit 214 based on instructions to switch displays from the remote controller 102.

[1.4. Summary]

As above, the method for presenting information displayed on the HMD 100 in the endoscope system 1 according to the present embodiment is described. According to the present embodiment, the notification unit 170 is controlled depending on information that a wearer of the HMD 100 is visually recognizing, and a non-wearer is notified of the information that the wearer of the HMD 100 is visually recognizing. In this way, the non-wearer can grasp what the wearer of the HMD 100 who is working in collaboration is viewing at present during the work. In such circumstances, a conversation is made and instructions are given, and therefore, it is made possible to easily establish communication between users, and the occurrence of loss in cooperation and the like can be avoided.

2. Second Embodiment

Figure 9:
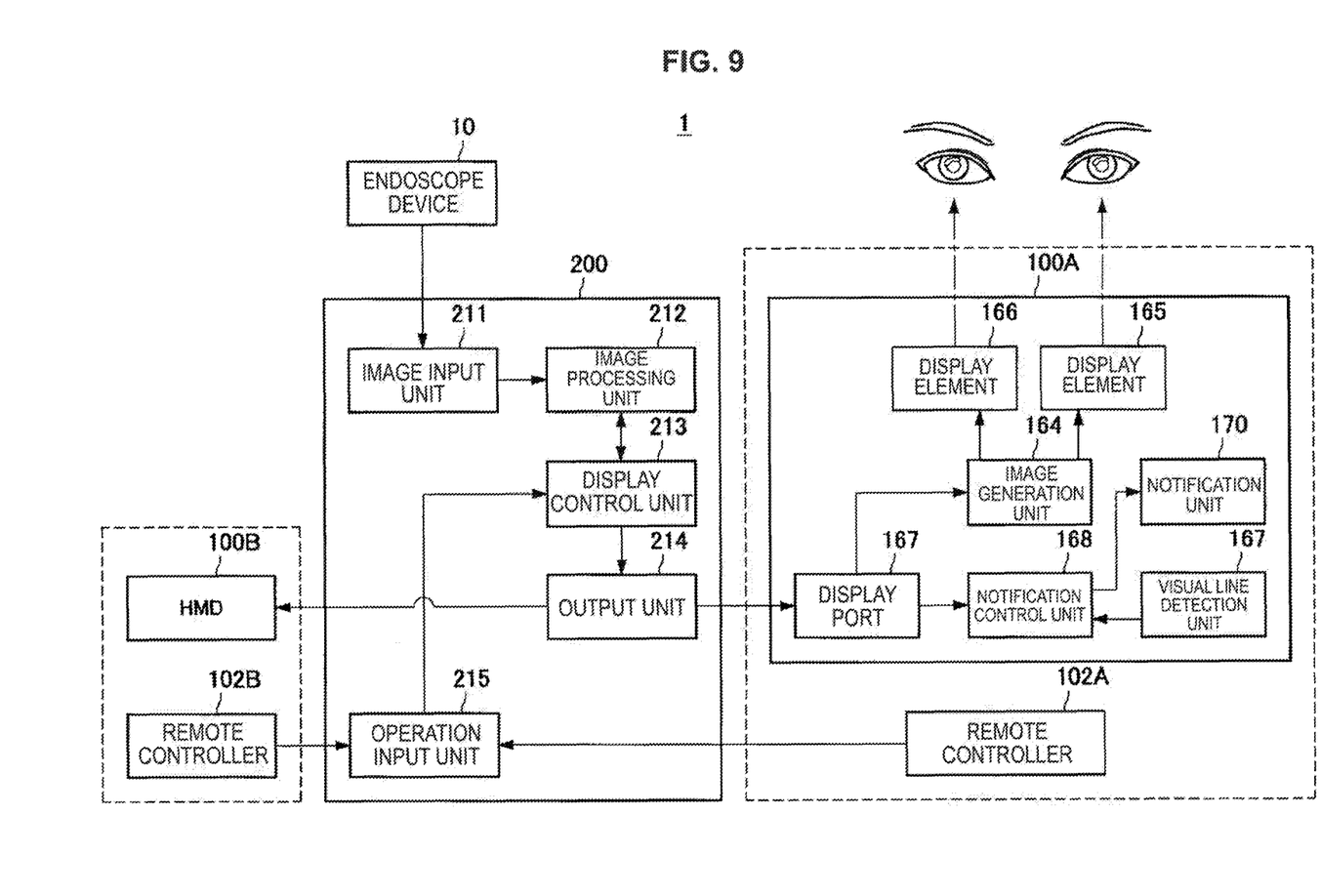
FIG. 9 is a function block diagram showing a function configuration of an HMD and a processor unit constituting a display control system according to a second embodiment of the present disclosure.

Next, based on FIG. 9, display control in a system that uses an HMD according to a second embodiment of the present disclosure is described. In the present embodiment, the endoscope system is described as an example, as in the first embodiment. FIG. 9 is a function block diagram showing a function configuration of the HMD 100 and the processor unit 200 constituting the endoscope system 1 according to the present embodiment. FIG. 9 shows the function units that function when display control of the display units 152 and 154 of the HMD 100 is performed and a notification control function of the HMD 100, but it is assumed that other function units are included actually.

Also in the example in FIG. 9, as in FIG. 8 of the first embodiment, the processor unit 200 functions as the display control device that performs display control of the two HMDs 100A and 100B and switches information that is presented to each HMD based on instructions to switch displays of each of the HMDs 100A and 100B. The configuration of the endoscope system 1 according to the present embodiment differs from the configuration of the first embodiment shown in FIG. 8 in that the HMD 100 includes a visual line detection unit 167. The other function units are the same as those of the first embodiment, and therefore, description of these function units is omitted.

The visual line detection unit 167 provided in the HMD 100 detects a visual line of a wearer of the HMD 100. The visual line detection unit 167 captures an image of the eyes of the wearer of the HMD 100 and detects the visual line from the positional relationship between a reference point and a moving point in the eyes. The visual line of the wearer detected by the visual line detection unit 167 is output to the notification control unit 168. The notification control unit 168 determines, on the basis of a detection result obtained by the visual line detection unit 167, whether the wearer is viewing the display units 152 and 154 or the wearer is viewing another part such as his/her hand(s). Then, on the basis of the determination result, the notification control unit 168 controls the notification unit 170 and notifies the non-wearer of the information that the wearer is viewing.

In this way, by detecting the visual line of the wearer by the visual line detection unit 167, for example, it is possible to grasp whether or not the wearer is viewing the display units 152 and 154 of the HMD 100. When there is a gap between the main body unit 110 and the eyes of the wearer and the lower part thereof is opened as in the HMD 100 shown in FIG. 2, there is a case where the person wearing the HMD 100 is able to view something other than the information displayed on the display units 152 and 154. At this time, if the wearer notifies a non-wearer of the information displayed on the display units 152 and 154, the recognition differs between the users and circumstances where communication is not established smoothly are conceivable.

Further, for example, as in PinP (Picture In Picture), in the case where another display region for displaying information is provided within the display region of the display units 152 and 154, the wearer moves his/her visual line to gaze the information in each display region. At this time, if the wearer notifies a non-wearer of the information displayed in the display region that the non-wearer is not viewing, recognition will also differ between the users.

As described above, the information that a wearer is visually recognizing is not necessarily limited to the information displayed on the display units 152 and 154 of the HMD 100. Information that a wearer is visually recognizing includes, for example, in addition to the main information displayed on the display units 152 and 154, information when the wearer views his/her hand(s) and information in one of display regions in the case where a plurality of display regions exists in the display units 152 and 154. Consequently, as in the present embodiment, the visual line detection unit 167 is provided in the HMD 100 and information that a wearer of the HMD 100 is visually recognizing is specified from the visual line of the wearer. Due to this, it is made possible to more exactly notify the non-wearer of the information that the wearer views, and therefore, it is possible to improve the communication between the users.

As above, the method for presenting information displayed on the HMD 100 in the endoscope system 1 according to the present embodiment is described. According to the present embodiment, the notification unit 170 is controlled depending on information that a wearer of the HMD 100 is visually recognizing, and a non-wearer is notified of the information that the wearer of the HMD 100 is visually recognizing. In this way, the non-wearer can grasp what the wearer of the HMD 100 who is working in collaboration is viewing at present during the work. In such circumstances, a conversation is made and instructions are given, and therefore, it is made possible to easily establish communication between users and the occurrence of loss in cooperation and the like can be avoided.

3. Modified Examples

In the embodiments described above, the notification of the information that a wearer of the HMD 100 is visually recognizing is performed by the notification unit 170 provided in the HMD 100, but the present disclosure is not limited thereto. For example, the notification unit 170 performing the notification of information that each wearer is visually recognizing may be provided in the processor unit 200.

To be specific, a notification unit such as a lamp or a display device may be provided in the processor unit 200, and the notification unit shows information that the wearer of the HMD 100 is visually recognizing, the HMD 100 being connected by the notification unit. In this way, it becomes possible to grasp all pieces of information that a plurality of wearers each wearing the HMD 100 by viewing the processor unit 200.

As above, the preferred embodiments of the present disclosure are described in detail with reference to the appended drawings, but the technical scope of the present disclosure is not limited to those examples. It is obvious that a person with ordinary knowledge in the technical field of the present disclosure may think out various kinds of altered examples or modified examples in the category of the scope of the technical idea described in the claims and those are of course construed to be included in the technical scope of the present disclosure.

For example, although the notification control unit 168 for controlling the notification unit 170 of the HMD 100 and the visual line detection unit 167 according to the above embodiments are provided in each HMD 100, the present technology is not limited thereto. For example, a function of a notification control unit or a visual line detection unit may be provided to the processor unit 200.

Further, in the above-described embodiments, the organic EL element is used as the display element, but the present technology is not limited to those examples. For example, a liquid crystal display element (LCD) may be used as the display element.

In addition, although it has been described in the above embodiments that a non-wearer is notified of information that a wearer of the HMD 100 is visually recognizing by the notification unit 170 of the HMD 100, the present technology is not limited thereto. For example, if the HMD 100 is of a see-through type, the wearer can visually recognize the notification unit 170 of the HMD 100 of another wearer. In this way, using the HMD of the see-through type, the wearer views the notification unit 170 of the other wearer via the image capturing unit 112 and thus can visually recognize the information that the other wearer is visually recognizing. In this way, communication between the wearer of the HMD 100 and a person other than the wearer can be improved.

The effects described in the present specification are only explanatory or illustrative but not limitative. The technology according to the present disclosure may bring about other effects obvious to the persons in the art from the description of the present specification together with the above-described effects or in place of the above-described effects.

Additionally, the present technology may also be configured as below.

(1) A head mounted display, including:
a display unit configured to present an image to a wearer;
a mounting unit configured to be mounted on a head of the wearer; and
a notification unit configured to notify a person other than the wearer of information that the wearer is visually recognizing.

(2) The head mounted display according to (1),
wherein the notification unit includes one or a plurality of lamps.

(3) The head mounted display according to (2),
wherein the notification unit performs notification of the information that the wearer is visually recognizing on a basis of at least one of a color of each of the one or the plurality of lamps, a lighting state of each of the one or the plurality of lamps, a number of the one or the plurality of lamps, and an amount of light emitted from each of the one or the plurality of lamps.

(4) The head mounted display according to (1),
wherein the notification unit is a display device configured to display information that the wearer is visually recognizing.

(5) The head mounted display according to (1),
wherein the notification unit is a display device configured to display corresponding information representing information that the wearer is visually recognizing.

(6) The head mounted display according to (5),
wherein the display device is capable of being curved.

(7) The head mounted display according to any one of (1) to (6),
wherein the information that the wearer is visually recognizing includes at least an image captured by an endoscope device.

(8) The head mounted display according to any one of (1) to (7), further including:
a notification control unit configured to control the notification unit on a basis of information that the wearer is visually recognizing.

(9) The head mounted display according to (8),
wherein the notification unit includes the one or a plurality of lamps, and
wherein the notification control unit controls, on a basis of information that the wearer is visually recognizing, at least one of a color of each of the one or the plurality of lamps, a lighting state of each of the one or the plurality of lamps, a number of the one or the plurality of lamps, and an amount of light emitted from each of the one or the plurality of lamps.

(10) The head mounted display according to (8) or (9), further including:
a visual line detection unit configured to detect a visual line of a wearer,
wherein the notification control unit determines, on a basis of a detection result obtained by the visual line detection unit, information that a wearer is visually recognizing.

(11) A control device, including:
a visually recognized information acquisition unit configured to acquire information that a wearer of a head mounted display is visually recognizing; and
a notification control unit configured to control a notification unit on a basis of information that the wearer is visually recognizing, the notification unit being included in the head mounted display and notifying a person other than the wearer of information that the wearer is visually recognizing.

(12) A control method, including:
acquiring information that a wearer of a head mounted display is visually recognizing; and
controlling a notification unit on a basis of information that the wearer is visually recognizing, the notification unit being included in the head mounted display and notifying a person other than the wearer of information that a wearer is visually recognizing.

REFERENCE SIGNS LIST 1 endoscope system
100 HMD
102 remote controller
110 main body unit
152 first display unit
154 second display unit
162 display port
164 image generation unit
165 first display element
166 second display element
167 visual line detection unit
168 notification control unit
170 notification unit
200 processor unit
211 image input unit
212 image processing unit
213 display control unit
214 output unit
215 operation input unit
300 display
400 external device

The invention claimed is:
1. A head mounted display, comprising:
a main body;
a fixing element that supports the main body on a head of a wearer; and
circuitry configured to:
control a display unit to display an image to the wearer; and
notify, information that the wearer is in a visually recognizing state to a person other than the wearer, by a plurality of light emitting elements of the head mounted display,
wherein the plurality of light emitting elements include a plurality of lamps, and
wherein the information is notified based on at least one of a number of the plurality of lamps or an amount of light emitted from each of the plurality of lamps.

2. The head mounted display according to claim 1, wherein the circuitry is further configured to control display of the information that the wearer is in the visually recognizing state.

3. The head mounted display according to claim 1, further comprises a display device configured to display corresponding information representing the information that the wearer is in the visually recognizing state.

4. The head mounted display according to claim 3, wherein the display device is curved.

5. The head mounted display according to claim 1, wherein the information that the wearer is in the visually recognizing state includes at least an endoscopic image captured by an endoscope device.

6. The head mounted display according to claim 1, wherein the circuitry is further configured to:
detect a visual line of the wearer, and determine, based on the detected visual line, the information that the wearer is in the visually recognizing state.

7. A control device, comprising:
circuitry configured to:
acquire information that a wearer of a head mounted display is in a visually recognizing state;
notify, by a plurality of light emitting elements of the head mounted display, a person other than the wearer of the information that the wearer is in the visually recognizing state,
wherein the plurality of light emitting elements include a plurality of lamps, and wherein the information is notified based on at least one of a number of the plurality of lamps or an amount of light emitted from each of the plurality of lamps.

8. A control method, comprising:
in a head mounted display:
   acquiring information that a wearer of a head mounted display is in a visually recognizing state; and
   notifying, by a plurality of light emitting elements of the head mounted display, a person other than the wearer of the information that the wearer is in the visually recognizing state,
   wherein the plurality of light emitting elements include a plurality of lamps, and
   wherein the information is notified based on at least one of a number of the plurality of lamps or an amount of light emitted from each of the plurality of lamps.

9. The head mounted display according to claim 1, wherein at least one of the plurality of light emitting elements is on a center of an external surface of the head mounted display such that the plurality of light emitting elements are visually recognizable by the wearer.

10. The head mounted display according to claim 1, wherein the circuitry is further configured to control the plurality of light emitting elements based on the wearer is viewing one of an endoscopic image that is captured by an endoscope device or an image that is captured by an external device, and wherein the external device is different from the endoscope device.

* * * * *